United States Patent [19]
Melmed et al.

[11] Patent Number: 5,972,893
[45] Date of Patent: Oct. 26, 1999

[54] METHOD OF TREATING HYPERPROLACTINEMIA AND PROLACTINOMAS

[75] Inventors: Shlomo Melmed, Los Angeles; Ilan Shimon, Beverly Hills, both of Calif.; Michael D. Culler, Hopkinton, Mass.

[73] Assignee: Cedars-Sinai Medical Center, Los Angeles, Calif.

[21] Appl. No.: 08/852,221

[22] Filed: May 6, 1997

[51] Int. Cl.$^6$ .............................. A61K 38/08; C07K 7/00
[52] U.S. Cl. ................. 514/16; 514/9; 530/317; 530/328; 435/69.1
[58] Field of Search .................... 530/317, 328; 514/9, 16; 435/69.1

[56] References Cited

U.S. PATENT DOCUMENTS

| | | | |
|---|---|---|---|
| 5,424,289 | 6/1995 | Yang et al. | 514/12 |
| 5,686,418 | 11/1997 | Culler | 514/17 |

FOREIGN PATENT DOCUMENTS

| | | |
|---|---|---|
| 0 203 031 A2 | 11/1986 | European Pat. Off. . |
| WO 97/11962 | 4/1997 | WIPO . |

OTHER PUBLICATIONS

PCT International Search Report.
Shimon, I. et al., "Somatostatin Receptor Subtype Specificity in Human Fetal Pituitary Cultures", J. Clin. Invest., 99(4): 789–798, Feb. 1997.
Han et al., Can. Res. vol. 47, pp. 1566–1570, Mar. 1987.
Goodman & Gilman's (6th Ed. MacMillan Publishing Co. 1980) Chapter 1, pp. 5–7.
Redding et al PNASUSA 80 pp. 1078–1082 (Feb. 1983).
Koper et al. Canc. Res. 50 6238–42 (Oct. 1990).
Lamberts et al. Acta Endocrinol (Copenh) 1987 115 pp. 196–202.
Shimon et al. J. Clin Invest (Nov. 1997) 100 No. 9 pp. 2386–2392.

*Primary Examiner*—Bennett Celsa
*Attorney, Agent, or Firm*—Pretty, Schroeder & Poplawski

[57] ABSTRACT

A method of treating hyperprolactinemia in an animal, including a human, administers one or more somatostatin type-5 receptor agonist(s) to, for example, lower abnormally high levels of prolactin in the blood of the animal. A method of treating a subject, including a human, afflicted by a prolactinoma, administers one or more type-5 receptor selective agonist(s) to, for example, lower prolactin secretion and/or decrease tumor size in the subject.

44 Claims, No Drawings

METHOD OF TREATING HYPERPROLACTINEMIA AND PROLACTINOMAS

BACKGROUND OF THE INVENTION

1. Field of the Invention

This invention relates to the field of hyperprolactinemias, and prolactinomas. More specifically, this invention relates to the treatment of a subject afflicted with either condition, and the lowering of prolactin levels and/or the size of the tumor by administration of a selected family of pharmaceuticals.

2. Description of the Background

Prolactin hypersecretion, or hyperprolactinemia, may have anyone of a number of functional causes, including various neurogenic causes such as thoracic sensory nerve stimulation, stress, and psychogenic causes, various hypothalamic causes such as diffuse processes, granulomatous diseases, neoplasms, stalk section, empty sella, non-lactotropic cell pituitary tumors, and prostradiation treatment to sella, various pituitary causes such as prolactinomas and pituitary lactotropic cell hyperplasia, and various endocrine causes such as pregnancy, estrogen administration, hypothyroidism, and adrenal insufficiency. Prolactin hypersecretion may also be caused by the administration of drugs which impair dopamine secretion, such as psychotropic drugs, antihypertensive drugs, antiemetic drugs, $H_2$-receptor blockers, and opiates, among others.

Prolactinomas are pituitary tumors, in fact, the most common pituitary tumors, which are almost five times more common in women than in men. Some prolactinomas respond to, and may be treated with, the dopamine agonist, Bromocriptine. One-third of the patients afflicted with prolactinomas, however, do not respond to, and are therefore not treatable with, this drug. The latter are usually referred for pituitary surgery and/or, rarely, irradiation.

Somatostatin, also known as somatotropin release inhibiting factor or SRIF, is believed to exert its biological effect through a family of G-protein associated receptors provided with seven transmembrane domains. Somatostatin inhibits the secretion of growth hormone. Five subtypes of the somatostatin receptor (SSTR) have already been cloned, and named SSTR-1, SSTR-2, SSTR-3, SSTR-4, and SSTR-5. The SSTR-1, SSTR-2, and SSTR-5 receptors have been shown to be expressed by the human pituitary gland, and the SSTR-1, SSTR-2, SSTR-3 and SSTR-5 receptors by human pituitary adenomas.

A large number of somatostatin agonists have been synthesized, and shown to preferentially bind to selected subtypes of the somatostatin receptor (SSTR) (See, below). Up until now, only SSTR-2 selective somatostatin agonists were shown to inhibit prolactin secretion from normal fetal pituitary cultures.

Up to the present time, thus, it was not known which subtype(s) of the SSTR mediate(s) the regulation of prolactin production and secretion in the state of pathological hyperprolactinemia, such as that resulting, for example, from a prolactinoma.

SUMMARY OF THE INVENTION

The present invention relates to a method of treating hyperprolactinemia and/or a prolactinoma in a subject by administering to the subject, which may be a mammal, such as a human, a therapeutically effective amount of one or more somatostatin type-5 receptor (SSTR-5) agonist(s), such as a somatostatin type-5 selective agonist. This administration, for example, lowers abnormally high levels of prolactin in the subject's blood. In addition, when treating a prolactinoma, the present method, for example, lowers either tumor prolactin secretion and/or decreases tumor size, in the subject.

The present treatment is effective in subjects afflicted by hyperprolactenemia, and particularly those who have abnormally high levels of prolactin, for example, as a result of one or more of the following: a pituitary tumor such as a prolactinoma, hypothalamic and pituitary stalk disease, hyperthyroidism, postpartum lactation, decreased dopamine or dopamine inhibitory action, which may be caused by the administration of drugs such as opiates and psychotropic drugs, among others, stimuli that overcome the normal dopaminergic inhibition such as the administration of estrogen, decreased clearance of prolactin such as in renal failure or cirrhosis, seizures, and chest wall trauma, among others. Given that the present family of drugs lowers prolactin levels, it also consequently, treats the galactorrhea, amenorrhea, infertility, impotence, and/or hypogonadism, which many times accompany it.

While it is possible for the somatostatin agonist to be administered as the pure or substantially pure compound, it may also be presented as a pharmaceutical composition, formulation or preparation. The composition of the invention comprises one or more of a selected class of somatostatin agonists, and one or more pharmaceutically acceptable carriers for the agonists, and optionally other therapeutic agents. The somatostatin agonist may be formulated for administration by various routes, including by a parenteral route such as an intravenous, subcutaneous, or intramuscular route, or by implantation of a sustained release formulation, among others. The carrier must be "acceptable" in that it has to be compatible with, and stabilizing of, the active ingredient(s) of the formulation, and not deleterious to the subject to be treated.

Other features and advantages of the invention will be apparent from the following description of the preferred embodiments and from the claims.

DETAILED DESCRIPTION OF THE INVENTION

The present invention arose from a desire by the inventors to improve on prior art treatments for hyperprolactinemias associated with various causes, including prolactinomas. This invention, thus, relates to the discovery that SSTR-5 somatostatin agonists, but not SSTR-2 somatostatin agonists, are capable of reducing serum prolactin levels, and inhibiting prolactin secretion in a subject which is in a state of pathological hyperprolactinemia, such as in the case of a subject carrying a prolactinoma. This invention, therefore, provides a treatment for hyperprolactinemias in general, and of prolactinomas in particular, in animals, including mammals such as humans. The treatment of the invention counters by the administration of a selected group of pharmaceuticals the conditions afflicting the subject, and lowers prolactin blood levels and/or tumor size.

The present inventors are providing a method of treating hyperprolactinemia and/or a prolactinoma in a subject by administering to a subject, a therapeutically effective amount of one or more somatostatin type-5 receptor (SSTR-5) agonist(s), such as a somatostatin type-5 selective agonist. "Therapeutic amounts of the agonists of the invention are those which decrease the pituitary secretion of prolactin, or reduce serum prolactin levels to within about the normal range. Preferably, the amount of the SSTR-5 agonist administered is intended to reduce prolactin serum levels to about 0 to 50 ng/ml blood, as detected by an immunoradiometric assay (IRMA), or in some instances even above 50 ng/ml, and more preferably below 70 ng/ml blood. Still a more preferred therapeutic amount of the agonists of the invention are those that permit lowering the prolactin serum levels to about 2 to 30 ng/ml blood, and more preferably to about 5 to about 20 ng/ml blood. It is, however, to be understood, that although many subjects afflicted with hyperprolactinemia are highly responsive to the treatment of the invention, they respond to different degrees. Thus, where in patients with a large, invasive tumors and high serum prolactin levels, reductions of 20–60% and more are highly desirable, they are not always attained. In fact, the responses may be highly variable, and particularly favorable in the case of large, invasive tumors, particularly those normally observed in males. It is generally desirable to lower the prolactin serum levels to within the ranges described above, which are normal prolactin levels. A "therapeutic amount" of the agonist of the invention for the treatment of prolactinomas is meant as that dose which reduces the size of the tumor by at least about 30%, more preferably by about more than about 50%, and still more preferably by more than about 80% or more. In some instances, however, there is a complete or almost complete disappearance of the tumor, as detected by MRI. In general, the present treatment affords a reduction of about 4–50% of large tumors, 4–5 cm in diameter. In smaller tumors, of about 1 cm in diameter, this treatment may attain a significant reduction in size, detectable to about 2 mm. In some instances, smaller tumors may be less responsive than larger tumors to the present treatment. Thus, the amount of drugs administered in this invention, which is considered to be therapeutically effective clearly depends upon the condition being treated, the route of administration chosen, and the specific activity of the compound used. This is a matter which is ultimately best decided by the attending physician or veterinarian. In one embodiment, the somatostatin agonist is administered to the subject until the subject's prolactin level stabilizes to within normal levels, such as when the prolactinoma has been removed or ablated. In another embodiment, the somatostatin agonist may be administered, if necessary, for the lifetime of the patient.

Somatostatin and its Agonists

Somatostatin or SRIF has a 14 amino acid isoform (somatostatin-14) as well as a 28 amino acid isoform (somatostatin-28). See Wilson, J. & Foster, D., Williams Textbook of Endocrinology, p. 510 (7th. Ed., 1985). Somatostatin inhibits the secretion of growth hormone, and was originally isolated from the hypothalamus. See, Brazeau, et al., Science 179: 77 (1973). The native somatostatin has a very short lasting in vivo effect, because it is rapidly inactivated by endo- and exo-peptidases. Many novel analogs of somatostatin, such as peptides and non-peptidic compounds, have been prepared in order to enhance the duration of effect, and biological activity of this hormone, and selectivity for one or more particular subtype of somatostatin receptor. Such somatostatin analogues are called "somatostatin agonists" for the purposes of this patent.

As already indicated, various somatostatin receptors (SSTRs) have been isolated, among them SSTR-1, SSTR-2, SSTR-3, SSTR-4, and SSTR-5. The somatostatin agonist, therefore, may be a SSTR-1 agonist, SSTR-2 agonist, SSTR-3 agonist, SSTR-4 agonist, or a SSTR-5 agonist.

By 'somatostatin type-5 receptor agonist' or SSTR-5 agonist, is meant a compound which (1) has a high binding affinity, e. g., Ki less than 5 nM, and preferably less than 1 nM, for human SSTR-5, for example, as defined by the receptor binding assay described below, and (2) decreases prolactin levels in a patient, for example, as shown by the biological assay described below. Examples of somatostatin agonists are those covered by formulae or those specifically recited in the publications set forth below, all of which are hereby incorporated by reference.

Van Binst, G. et al., Peptide Research 5: 8 (1992);
Horvath, A., et al., Abstract, "Conformations of Somatostatin Analogs Having Antitumor Activity", 22nd. European peptide Symposium, Sep. 13–19, 1992, Interlaken, Switzerland;
EP Appl. No. P5 164 EU; PCT Appl. WO 91/09056 (1991);
EP Appl. No. 0 363 589 A2(1990); U.S. Pat. No. 4,904,642;
U.S. Pat. No. 4,871,717; U.S. Pat. No. 4,853,371;
U.S. Pat. No. 4,725,577; U.S. Pat. No. 4,684,620;
U.S. Pat. No. 4,650,787; U.S. Pat. No. 4,603,120;
U.S. Pat. No. 4,585,755; EP Appl. No.0 203 031 A2 (1986);
U.S. Pat. No. 4,522,813; U.S. Pat. No. 4,486,415;
U.S. Pat. No. 4,485,101; U.S. Pat. No. 4,435,385;
U.S. Pat. No. 4,395,403; U.S. Pat. No. 4,369,179;
U.S. Pat. No. 4,360,516; U.S. Pat. No. 4,358,439;
U.S. Pat. No. 4,328,214; U.S. Pat. No. 4,316,890;
U.S. Pat. No. 4,310,518; U.S. Pat. No. 4,291,022;
U.S. Pat. No. 4,238,481; U.S. Pat. No. 4,235,886;
U.S. Pat. No. 4,224,199; U.S. Pat. No. 4,211,693;
U.S. Pat. No. 4,190,648; U.S. Pat. No. 4,146,612;
U.S. Pat. No. 4,133,782; U.S. Pat. No. 5,506,339;
U.S. Pat. No. 4,261,885; U.S. Pat. No. 4,728,638;
U.S. Pat. No. 4,282,143; U.S. Pat. No. 4,215,039;
U.S. Pat. No. 4,209,426; U.S. Pat. No. 4,190,575;
EP Pat. No. 0 389 180; EP Appl. No. 0 505 680 (1982);
EP Appl. No. 0 083 305 (1982); EP Appl. No. 0 030 920 (1980);
PCT Appl. No. WO 88/05052; PCT Appl. No. WO 90/12811;
PCT Appl. No. WO 97/01579; PCT Appl. No. WO 91/18016;
UK Appl.No.GB 2,095,261 (1981); French Appl.No.FR2, 522,655(1983)

Examples of SSTR-5 agonists include, but are not limited to the following:
H-D-Phe-Cys-Tyr-D-Trp-Lys-Val-Cys-$\beta$-Nal-NH$_2$;
H-D-Phe-Cys-Tyr-D-Trp-Lys-Thr-Cys-$\beta$-Nal-NH$_2$; and
H-D-Phe-Cys-Tyr(I)-D-Trp-Lys-Val-Cys-Thr-NH$_2$.

By 'somatostatin type-5 receptor selective agonist is meant a somatostatin agonist which (1) has a higher binding affinity, or Ki, for SSTR-5 than for either SSTR-1, SSTR-2, SSTR-3, or SSTR4, and (2) decreases prolactin levels in a patient, for instance, as shown by the biological assay described below. In one embodiment, the SSTR-5 selective agonist has a Ki for SSTR-5 that is at least 2 times, and may be at least 10 times, less than its Ki for the SSTR-2 receptor. For example, as defined by the receptor binding assay described below. In another embodiment, the somatostatin type-5 receptor selective agonist is also a SSTR-5 agonist. Examples of SSTR-5 selective somatostatin agonists include, but are not limited to the following somatostatin analogs, which are disclosed in the above-cited references:
H-Cys-Phe-Phe-D-Trp-Lys-Thr-Phe-Cys-NH$_2$ (BIM-23268);
H-D-Phe-Phe-Phe-D-Trp-Lys-Thr-Phe-Thr-NH$_2$ (BIM-23052);
H-D-Phe-Phe-Tyr-D-Trp-Lys-Val-Phe-Thr-NH$_2$;
H-D-Tyr-Phe-Phe-D-Trp-Lys-Thr-Phe-Thr-NH$_2$;
H-D-Phe-Phe-Trp-D-Trp-Lys-Thr-Phe-Thr-NH$_2$;

H-D-Tyr-D-Phe-Tyr-D-Trp-Lys-Thr-Phe-Thr-NH$_2$;
H-D-Phe-Cpa-Tyr-D-Trp-Lys-Thr-Phe-Thr-NH$_2$;
H-D-Cys-Phe-Phe-D-Trp-Lys-Thr-Phe-Cys-NH$_2$;
H-Cys-Phe-Trp-D-Trp-Lys-Ser-Phe-Cys-NH$_2$;
H-Cys-Phe-Phe-D-Trp-Lys-Ser-Phe-Cys-NH$_2$;
H-Cys-Phe-Phe-D-Trp-Lys-Thr-Phe-Cys-NH$_2$;
H-Cys-Phe-Tyr-D-Trp-Lys-Thr-Phe-Cys-NH$_2$;
H-Cys-Phe-His-D-Trp-Lys-Thr-Phe-Cys-NH$_2$; and
H-Cys-Phe-Tyr(I)-D-Trp-Lys-Thr-Phe-Cys-NH$_2$.

It should be noted that for all somatostatin agonists represented above, each amino acid residue represents the structure of —NH—C(R)H—CO—, wherein R is the side chain of the amino acid (e.g., CH$_3$ for Ala). Lines between amino acid residues represent peptide bonds which join the amino acids. In addition, where the amino acid residue is optically active, it is the L-form configuration that is intended unless D-form is expressly designated. The abbreviations Cpa, β-Nal, and Tyr(I) stand for the amino acids p-Cl-Phe, 2-napthylalanine, and iodinated tyrosine (e.g., 3-I-Tyr, 5-I-Tyr, or 3,5-I-Tyr). Although a disulfide bridge forms between two free thiols of the Cys residues, this is not shown above. Preferred are the peptides BIM-23268 and BIM-23052, as well as their mixture or combination. However, any of the other agonists listed above are also within the four corners of this invention.

The present agonists may be administered alone, or in a composition, or separately but jointly with other therapeutic agents, including other prolactin inhibitors. In addition to lowering levels of prolactin in the subject's blood, when administered to a subject afflicted with a prolactinoma, the present method is very effective in lowering either tumor prolactin secretion and/or in decreasing tumor size, or both. The present treatment is, thus, highly effective in subjects afflicted by abnormally high levels of prolactin caused by, for example, one or more of the following conditions: a pituitary tumor such as a prolactinoma, hypothalamic and pituitary stalk disease, hyperthyroidism, postpartum lactation, decreased dopamine or dopamine inhibitory action, which may be caused by the administration of drugs such as opiates and psychotropic drugs, among others, stimuli that overcome the normal dopaminergic inhibition such as the administration of estrogen, decreased clearance of prolactin such as in renal failure or cirrhosis, seizures, and chest wall trauma, among others.

In addition to lowering serum prolactin levels, the present family of drugs is also effective in the treatment of galactorrhea, amenorrhea, infertility, impotence, and/or hypogonadism, which many times are associated with increased prolactin levels.

The somatostatin agonist(s) of this invention may be administered as a purified, or substantially purified compound, it may also be presented as a pharmaceutical composition, formulation or preparation. The composition of the invention comprises one or more of a selected class of somatostatin agonists, and one or more pharmaceutically acceptable carriers for the agonists, and optionally other therapeutic agents. Formulations of the somatostatin agonist (s) described herein encompass those custom tailored for administration by various routes, including by a parenteral route, which may be an oral, intravenous, subcutaneous, or intramuscular route, or by implantation of a sustained release formulation, among others. The carrier(s) must be "acceptable" in that it has to be compatible with, and stabilizing of, the active ingredient(s) of the formulation, and not deleterious to the subject to be treated ("pharmaceutically acceptable").

The formulation should preferably be free of oxidizing agents, or other substances with which peptides are known to be incompatible. Somatostatin agonists that are in their cyclized form, such as those that have an internal cysteine disulfide bond may, for example, be in their oxidized or reduced forms. Thus, the presence of a reducing agent in the composition might lead to an opening of the cysteine disulfide bridge. On the other hand, highly oxidative conditions may, for example, lead to the formation of cysteine sulfoxide, and to the oxidation of tryptophan. It is, therefore, of great importance that excipients and other components of the formulation be carefully select. The pH of the composition is also of import, and it is preferable that the product be buffered under slightly acidic conditions, such as pH about 5 to about 6. These pHs, however, are not limiting.

In general, the formulations for tablets or powders may be prepared by uniformly and intimately blending the active ingredient with finely divided solid carriers, and then, if necessary, as in the case of tablets, forming the product into the desired shape and size.

Formulations suitable for parenteral, e.g., intravenous, administration, on the other hand, conveniently comprise sterile aqueous solutions of the active ingredient(s). The solutions are, preferably, isotonic with the blood of the subject to be treated. Such formulations may. For example, be conveniently prepared by dissolving solid active ingredient(s) in water or another aqueous solvent to produce an aqueous solution, and rendering the solution sterile. These and other formulation may be presented in unit or multi-dose form, in containers, for example, sealed ampoules or vials, among others. The formulation may be prepared by any of the well known methods to the pharmaceutical artisan. All methods include the step of bringing the active ingredient(s) into association with the carrier, which constitutes one or more accessory ingredients. Sustained release formulations suitable for parenteral administrations, such as biodegradable polymer formulations, for example, those including polyesters containing lactic or glycolic acid residues, are also well known in the art. See, e.g., U.S. Pat. Nos. 3,773,919 and 4,767,628 and PCT Publication No. WO 94/15587.

The somatostatin agonist of the invention or its composition may also be administered with another compound capable of lowering blood levels of prolactin, including dopamine agents such as Bromocriptine, cabergoline, pergolide, or lisuride, among others. This compounds may be added to the same composition, or administered separately in amounts that are known in the art. In some instances, when administered in joint therapy with the agonist(s) of this invention, the amounts of the latter compounds administered will be lower than the doses which are utilized when they are administered by themselves. In other instances, however, similar doses may be utilized, which will be additive or potentiating of the present treatment.

The somatostatin agonist may be injected parenterally, e.g., intravenously, into the bloodstream of the subject being treated. It will, however, be readily appreciated by those skilled in the art that which route, whether intravenous, subcutaneous, intramuscular, intraperitoneal, enterally, transdermally, transmucously, sustained released polymer compositions, e. g., lactic acid polymer or lactic acid and glycolic acid copolymer microparticle or implant, perfusion, nasal, oral, etc., will depend on the condition being treated, and the activity and bioavailability of the somatostatin agonist being used.

It is believed that one skilled in the art may, based on the description provided herein, utilize the present invention to its fullest extent. The following specific embodiments are, therefore, to be construed as merely illustrative, and not limiting of the remainder of the disclosure in any way or manner.

Unless defined otherwise, all technical and scientific terms used herein have the same meaning as commonly understood by one of ordinary skill in the art to which this invention belongs. All publications, patent applications, patents, and other references mentioned herein to enable different aspects of the invention are incorporated into the present text by reference to the extent necessary to attain the desired goal.

The invention will now be described with reference to some specific examples, which are representative of the invention in general. These examples are solely exemplary, and not limiting of the invention in any form or mode.

EXAMPLES

Example 1
Synthesis of BIM-23052

The peptide H-D-Phe-Phe-Phe-D-Trp-Lys-Thr-Phe-Thr-NH2 (BIM-23052) described above may be synthesized by following the protocol set forth in Example I of European Pat. Appl. 0 395 417 A1.

Example 2
Synthesis of other Somatostatin Agonists

The methods for synthesizing somatostatin agonists are well documented and are within the ability of a person of ordinary skill in the art. In addition, the synthesis of short amino acid sequences is well established in the peptide art. The syntheses of cyclic somatostatin analogs are described earlier cited patents/patent applications referenced in the prior subsection (e.g., U.S. Pat. No. 4,904,642 (2/90)). The synthesis of somatostatin agonists with a substituted N-terminus may be achieved, for example, by following the protocol set forth in WO 88/02756 (4/88), European Pat. Appl. No. 0 329 295 (8/89), and PCT Publication No. WO 94/04752 (3/94).

Example 3
Isolation of Somatostatin Receptor DNA

The human SSTR-1, SSTR-2, SSTR-3, SSTR4, and SSTR-5 cDNA clones have been described (SSTR-1 and SSTR-2: Yamada, Y., et al., P.N.A.S. USA, 89: 251–255 (1992); SSTR-3: Yamada, et al., Mol. Endocrinol. 6: 2136–2142 (1993); and SSTR-4 and SSTR-5: Yamada, et al., B.B.R.C. 195: 844–852 (1993)). The actual clones for the SSTR-1 to -3 are available from the American Type Culture Collection (ATCC, Rockville, Md.), under the Accession Nos. ATCC Nos. 79044 (SSTR-1), 79046 (SSTR-2), and 79048 (SSTR-3)).

Based on the restriction endonuclease maps, the entire coding region of each SSTR cDNA may be excised by suitable restriction endonuclease digestion (See, Maniatis, T., et al., Molecular Cloning-A Laboratory Manual, CSHL, (1982)). Restriction endonucleases are available, e.g., from New England Biolabs (Beverly, Mass.). The present cDNA fragment was inserted into the mammalian expression vector, pCMV (Russell, D., et al., J. Biol.

Chem., 264: 8222–8229 (1989)), using standard molecular biology techniques (See, e.g., Maniatis, T., et al., Molecular Cloning,—A Laboratory Manual, Cold Spring Harbor Laboratory (1982)), to produce the expression plasmid, pCMV-human SSTR-1 through pCMV-human SSTR-5.

Other mammalian expression vectors suitable for use herein include pcDNA1/Amp (Invitrogen, Sandlesy, Calif.). The expression plasmids were introduced into the suitable bacterial host, E. Coli HB101 (Stratagene, La Jolla, Calif.) and plasmid DNAs, for transfection, were prepared on Cesium Chloride gradients.

Example 4
Cell Transfection with Hybrid Vector

CHO-K1 (ovary, Chinese hamster) cells were obtained from ATCC (ATCC No. CCL 61). The cells were grown and maintained in Ham's F12 media (Gibco BRL, Grand Island, N.Y.) supplemented with 10% fetal bovine serum under standard tissue culture conditions. For transfection, the cells were seeded at a density $1\times10^6$/60-cm plate (Baxter Scientific Products, McGaw Park, Ill.). DNA mediated transfection was carried out using the calcium phosphate co-precipitation method (Ausubel, F. M., et al., Current Protocols in Molecular Biology, John Wiley & Sons, 1987). The plasmid pRSV-neo (ATCC; ATCC No. 37198) was included as a selectable marker at 1/10 the concentration of the expression plasmid. CHO-K1 clonal cell lines that have stably inherited the transfected DNA were selected for growth in Ham's F12 media containing 10% fetal bovine serum and 0.5 mg/ml of G418 (Sigma). The cells were ring-cloned and expanded in the same media for analysis.

Example 5
Cell Expression of Somatostatin Receptors

Expression of the human SSTR-1 through SSTR-5 receptors in the CHO-K1 cells were detected by Northern blot analysis of total RNA prepared from the cells (Sambrook, J. E., et al., Molecular Cloning—A Laboratory Manual, Ed. 2., Cold Spring Harbor Laboratory, Cold Spring Harbor, N.Y., 1989) and by receptor binding using $[^{125}\text{I-Tyr}^{11}]$ somatostatin-14 as a ligand. Transfected cell lines expressing the human SSTR receptors were clonally expanded in culture and used in the following SSTR binding protocol.

Example 6
Preparation of Receptor-containing Membranes

Crude membranes were prepared by homogenization of the transfected cells in 20 ml of ice-cold 50 mM Tris-HCl with a POLYTRON homogenizer (setting 6, 15 sec). Buffer was added to obtain a final volume of 40 ml, and the homogenate was centrifuged in a Sorval SS-34 rotor at 39,000 g for 10 min at 0–4° C. The resulting supernatant was decanted and discarded. The pellet was re-homogenized in ice-cold buffer, diluted, and centrifuged as before. The final pellet was resuspended in the 10 mM Tris HCl and held on ice for the receptor binding assay.

Example 7
Somatostatin Receptor Binding Assay

Aliquots of the membrane preparation were incubated for 30 min at 30° C. with 0.05 nM $[^{125}\text{I-Tyr11}]$ somatostatin-14 (2000 Ci/mmol; Amersham Corp., Arlington Heights, Ill.) in 50 mM HEPES (pH 7.4) containing a test somatostatin agonist of various concentrations (e.g., $10^{-11}$ to $10^{-6}$), 10 mg/ml bovine serum albumin (fraction V) (Sigma Chemical Co., St. Louis, Mo.), $MgCl_2$ (5 mM), Trasylol (200 KIU ml), bacitracin (0.02 mg/ml), and phenylmethylsulphonyl fluoride (0.02 mg/ml). The final assay volume was 0.3 ml. The incubations were terminated by rapid filtration through GF/C filters (pre-soaked in 0.3% polyethylenimine for 30 min) using a Brandel filtration manifold. Each tube and filter were then washed three times with 5 ml aliquots of ice-cold buffer.

Specific binding is defined as the total $[^{125}\text{I-Tyr}^{11}]$SRIF-14 bound minus that bound in the presence of 1000 nM. The Ki values for the tested somatostatin agonists were calculated by using the following formula: $Ki=IC_{50}/[1+(LC/LEC)]$ where $IC_{50}$ is the concentration of test somatostatin agonist required to inhibit 50 percent of the specific binding of the radioligand $[^{125}\text{I-Tyr11}]$ somatostatin-14, LC is the concentration of the radioligand (0.05 nM), and LEC is the equilibrium dissociation constant of the radioligand (0.16 nM). The Ki values (nm) for the tested somatostatin agonists are shown in Table I below.

TABLE I

Ki (nm) for Selected Somatostatin Agonists

|  | hSSTR-1 | hSSTR-2 | hSSTR-3 | hSSTR-4 | hSSTR-5 |
|---|---|---|---|---|---|
| Somatostatin-14 | 2.26 | 0.23 | 1.2 | 1.8 | 1.41 |
| Somatostatin-28 | 2.38 | 0.30 | 1.3 | 7.93 | 0.4 |
| Lanreotide | 2414 | 0.75 | 97.9 | 1826 | 5.21 |
| BIM-23268 | 1227 | 15.06 | 545 | 3551 | 0.42 |
| BIM-23052 | 97.6 | 11.96 | 5.6 | 127 | 1.22 |
| Octreotide | 875 | 0.57 | 26.8 | 5029 | 6.78 |
| BIM-23190 | 9120 | 0.35 | 215 | 7537 | 11.1 |
| BIM-23197 | 6016 | 0.19 | 26.8 | 3897 | 9.81 |
| BIM-23023 | 6616 | 0.43 | 869 | 2700 | 4.18 |

*Subtype affinity was determined by radioligand membrane receptor binding assays in CHO cells expressing human SSTR2 gene or SSTR -5 cDNA, as described by Shimon, I., et al., J. Clin. Invest. 99:789 (1997).

Example 8
Reduction of Prolactin Secretion from Prolactinomas

Cells derived from six prolactin-secreting pituitary adenomas were treated with somatostatin agonists with different binding selectivities for SSTR-2 and SSTR-5. Tumor specimens were cultured as described as described by Shimon, I. et al. (1997) (See, Table II below). Briefly, the specimens were washed in DME with 0.3% BSA, minced and enzymatically dissociated using 0.35% collagenase and 0.1% hyaluronidase (Sigma Chemical Co., St. Louis, Mo.) for 1 hour. The cell suspensions were filtered and resuspended in low glucose DME with 10% FBS and antibiotics before seeding in 48-well tissue culture plates (~5×104 cells/well; 50–80 wells/tumor) in 0.5 ml medium for 96 hours.

The medium was changed before treatment to serum-free defined DME, and the cell cultures were treated for 3 hours with 10–100 nM of the type 2-selective somatostatin agonists BIM-23014 (Lanreotide), BIM-23023, BIM-23190, and BIM-23197, the sequences of which are disclosed in Moreau, et al., Metabolism 45(8): 24 (1996), and the type-5 selective somatostatin agonists BIM-23268 and BIM-23052. (6–8 wells for each analog or control (vehicle solution only)), after which medium was frozen for later hormone measurements.

Example 9
Treatment of Adenoma Cells with Somatostatin Type-5 Agonists in Accordance with the Invention Six prolactin-secreting pituitary adenomas were obtained, cultured, and treated with analogues representative of the somatostatin analogues of the invention. Adenoma cells were obtained from large macroprolactinomas of 4 male patients (Patient Tumors 1, 2, 3, and 4). Three of the macroprolactinomas were invasive, and were accompanied by serum prolactin levels over 1,000 ng/ml. The cells from all 4 different tumors responded to treatment with the SSTR-5 selective agonists BIM-23052 or BIM-23268 with suppression of prolactin secretion.

The SSTR-5 type selective somatostatin agonists BIM-23052 and BIM-23268 (10 nM) suppressed prolactin secretion by 33 and 36%, respectively (p<0.05), in cell cultures from tumor 1. In contrast, the SSTR-2 selective somatostatin agonists Laureotide, BIM-23023, BIM-23190, and BIM-23197, did not affect prolactin release from the adenomatous cell cultures of tumor 1.

Prolactin release from tumor 2 cell cultures were inhibited by treatment with 10 nM BIM-23268 (38% versus controls; p<0.0005).

Large tumor 3 cell cultures were treated with 10 nM and 100 nM of the SSTR-5 selective somatostatin agonist BIM-23268. The type-5 agonist BIM-23268 suppressed prolactin in a dose dependent manner by up to 29% (p<0.05).

Large tumor 4 cell cultures suppressed prolactin release in response to both BIM-23052, and BIM-23268 by more than 30% (p<0.05), whereas BIM-23190, and BIM-23197 modestly stimulated prolactin production.

The four large male tumors also failed to respond to commercially available drugs, such as Octrotide, and Lanreotide, as well as to novel agonists with even higher affinities for the SSTR-2, including BIM-23190, and BIM-23197.

Small non-invasive prolactin-secreting tumors were obtained from female patients 5 and 6, who had circulating prolactin levels of less than 200 ng/ml serum. These cells failed to significantly respond to any of the somatostatin agonists examined. The clinical characteristics of the patients are shown in Table III below.

TABLE III

Clinical Characteristics of Six Prolactinoma Patients

| No. | Sex | Age | PRL ng/ml | Tumor Size (cm) | DA Therapy | Indication for surgery | In vitro SSTR5 Response |
|---|---|---|---|---|---|---|---|
| 1 | M | 64 | 742 | 1.5 non-invasive | none | patient preference | + |
| 2 | M | 33 | 1249 | 3.0 invasive | bromocriptine | drug compliance | + |
| 3 | M | 41 | 1514 | >3.0 invasive | bromocriptine | DA resistance | + |
| 4 | M | 33 | 2862 | 3.4 invasive | bromocriptine | DA resistance | + |
| 5 | F | 29 | 67 | 2.7 non-invasive | none | patient preference | − |
| 6 | F | 27 | 150 | 0.9 non-invasive | bromocriptine | DA resistance | − |

DA, dopamine agonist.

Human prolactin (PRL) levels were measured by immunoradiometric assay (obtained from Diagnostic Products Corporation, Los Angeles, Calif.) after appropriate sample dilution, as described by Shimon I., et al., J. Clin. Invest. 99: 789–798 (1997).

DA, dopamine agonist.

Having now described the invention in general, and by reference to specific examples, it is understood that many variations of the above may be practiced by an artisan based on the above disclosure, which are within the scope of the invention, and of the following claims. The foregoing description has been limited to specific embodiments of this invention. It will be apparent, however, that these variations and modifications made to the invention, with the ensuing attainment of some or all of the advantages of the inventions, are also within the scope of the following claims.

What is claimed as novel and unobvious in United States Letters Patent is:

1. A method of treating hyperprolactinemia in a subject, comprising administering to a subject in need of the treatment a therapeutically effective amount of a somatostatin type-5 receptor (SSTR type-5) agonist having a Ki for the type-5 somatostatin receptor of <5 nM and at least 10 times lower than its Ki for the somatostatin type-2 receptor, wherein $Ki=IC_{50}(1+(LC/LEC))$, $IC_{50}$ is the concentration of somatostatin agonist required to inhibit 50 percent of the specific binding of the radioligand $^{125}I$-$Tyr^{11}$ somatostatin-14; LC is the concentration of the radioligand; and LEC is the equilibrium dissociation constant of the radioligand.

2. The method of claim 1, wherein the somatostatin type-5 receptor agonist has a Ki less than 1 nM for the somatostatin type-5 receptor.

3. The method of claim 1, wherein the somatostatin type-5 receptor agonist is administered by an oral, intravenous, subcutaneous, intramuscular, nasal, intraperitoneal, perfusion, enteral, transdermal or transmucous route.

4. The method of claim 1, wherein the type-5 receptor agonist comprises a peptide selected from the group consisting of H-Cys-Phe-Phe-D-Trp-Lys-Thr-Phe-Cys-NH$_2$,
H-D-Phe-Phe-Phe-D-Trp-Lys-Thr-Phe-Thr-NH$_2$,
H-D-Phe-Cys-Tyr-D-Trp-Lys-Val-Cys-β-Nal-NH$_2$,
H-D-Phe-Cys-Tyr-D-Trp-Lys-Thr-Cys-β-Nal-NH$_2$,
H-D-Phe-Phe-Tyr-D-Trp-Lys-Val-Phe-Thr-NH$_2$,
H-D-Tyr-Phe-Phe-D-Trp-Lys-Thr-Phe-Thr-NH$_2$,
H-D-Phe-Phe-Trp-D-Trp-Lys-Thr-Phe-Thr-NH$_2$,
H-D-Tyr-D-Phe-Tyr-D-Trp-Lys-Thr-Phe-Thr-NH$_2$,
H-D-Phe-Cpa-Tyr-D-Trp-Lys-Thr-Phe-Thr-NH$_2$,
H-D-Cys-Phe-Phe-D-Trp-Lys-Thr-Phe-Cys-NH$_2$,
H-Cys-Phe-Trp-D-Trp-Lys-Ser-Phe-Cys-NH$_2$,
H-Cys-Phe-Phe-D-Trp-Lys-Ser-Phe-Cys-NH$_2$,
H-Cys-Phe-Phe-D-Trp-Lys-Thr-Phe-Cys-NH$_2$,
H-Cys-Phe-Tyr-D-Trp-Lys-Thr-Phe-Cys-NH$_2$,
H-Cys-Phe-His-D-Trp-Lys-Thr-Phe-Cys-NH$_2$,
H-Cys-Phe-Tyr(I)-D-Trp-Lys-Thr-Phe-Cys-NH$_2$, and mixtures thereof.

5. The method of claim 1, wherein the type-5 receptor agonist comprises H-Cys-Phe-Phe-D-Trp-Lys-Thr-Phe-Cys-NH$_2$.

6. The method of claim 1, wherein the type-5 receptor agonist comprises H-D-Phe-Phe-Phe-D-Trp-Lys-Thr-Phe-Thr-NH$_2$.

7. The method of claim 1, wherein the amount of the agonist administered is effective to lower prolactin levels to within about 0 to about 50 ng/ml blood, when measured by immunoradiometry.

8. The method of claim 7, wherein the amount of the agonist administered is effective to lower prolactin levels to within about 2 to about 30 ng/ml blood, when measured by immunoradiometry.

9. The method of claim 8, wherein the amount of the agonist administered is effective to lower prolactin levels to within about 5 to about 20 ng/ml blood, when measured by immunoradiometry.

10. The method of claim 1, further comprising administering to the subject an amount of a therapeutic agent selected from the group consisting of bromocriptine, cabergoline, pergolide, lisoride and mixtures thereof.

11. A method of treating a subject afflicted by hyperprolactinemia associated with postpartum lactation, comprising conducting the method of claim 1.

12. A method of treating a subject afflicted by hyperprolactinemia induced by drugs, comprising conducting the method of claim 1.

13. The method of claim 12, wherein the drug is selected from the group consisting of opiates and psychotropic drugs.

14. A method of treating a subject afflicted by hypothalamic or pituitary stalk disease associated with blood levels of prolactin above a normal range, comprising conducting the method of claim 1.

15. A method of treating a subject afflicted by hyperthyroidism associated with levels of serum prolactin above a normal range, comprising conducting the method of claim 1.

16. A method of treating a subject afflicted by decreased dopamine or dopamine inhibitory action associated with levels of serum prolactin above a normal range, comprising conducting the method of claim 1.

17. A method of treating a subject afflicted by a stimulus that overcomes normal dopaminergic inhibition associated with levels of serum prolactin above a normal range, comprising conducting the method of claim 1.

18. The method of claim 17, wherein the stimulus that overcomes normal dopaminergic inhibition comprises the administration of estrogen.

19. A method of treating a subject afflicted by decreased clearance of prolactin associated with levels of serum prolactin above a normal range, comprising conducting the method of claim 1.

20. A method of treating a subject afflicted by renal failure or cirrhosis associated with levels of serum prolactin above a normal range, comprising conducting the method of claim 1.

21. A method of treating a subject afflicted by seizures associated with levels of serum prolactin above a normal range, comprising conducting the method of claim 1.

22. A method of treating a subject afflicted by chest wall trauma associated with levels of serum prolactin above a normal range, comprising conducting the method of claim 1.

23. The method of claim 1, wherein the subject is human.

24. The method of claim 1, wherein the subject is afflicted by a prolactinoma.

25. The method of claim 24, wherein the somatostatin type-5 receptor agonist is administered by an oral, intravenous, subcutaneous, intramuscular, nasal, intraperitoneal, perfusion, enteral, transdermal or transmucous route.

26. The method of claim 24, wherein the amount of the somatostatin type-5 receptor agonist administered is effective for lowering the amount of prolactin secreted by the prolactinoma and maintaining within about normal blood levels of prolactin.

27. The method of claim 24, wherein the amount of the somatostatin type-5 receptor agonist is effective for lowering prolactin levels to within about 0 to about 50 ng/ml blood, when measured by immunoradiometry.

28. The method of claim 27, wherein the amount of the somatostatin type-5 receptor agonist is effective for lowering the prolactin levels to within about 2 to about 30 ng/ml blood, when measured by immunoradiometry.

29. The method of claim 28, wherein the amount of the somatostatin type-5 receptor agonist is effective for lowering the prolactin levels to within about 5 to about 20 ng/ml blood, when measured by immunoradiometry.

30. The method of claim 1, wherein the somatostatin type-5 receptor is administered as a sustained release formulation.

31. The method of claim 25, wherein the amount of a somatostatin type-5 receptor agonist is effective for lowering the amount of prolactin secreted by the prolactinoma.

32. The method of claim 31, wherein the Ki of the somatostatin type-5 receptor agonist for the type-5 somatostatin receptor is at least 10 times lower than its Ki for the somatostatin type-2 receptor.

33. The method of claim 24, wherein the somatostatin type-5 receptor agonist comprises a peptide selected from the group consisting of H-Cys-Phe-Phe-D-Trp-Lys-Thr-Phe-Cys-NH$_2$,
H-D-Phe-Cys-Tyr-D-Trp-Lys-Val-Cys-β-Nal-NH$_2$,
H-D-Phe-Cys-Tyr-D-Trp-Lys-Thr-Cys-β-Nal-NH$_2$,
H-D-Phe-Phe-Tyr-D-Trp-Lys-Val-Phe-Thr-NH$_2$,
H-D-Tyr-Phe-Phe-D-Trp-Lys-Thr-Phe-Thr-NH$_2$,
H-D-Phe-Phe-Trp-D-Trp-Lys-Thr-Phe-Thr-NH$_2$,
H-D-Tyr-D-Phe-Tyr-D-Trp-Lys-Thr-Phe-Thr-NH$_2$,
H-D-Phe-Cpa-Tyr-D-Trp-Lys-Thr-Phe-Thr-NH$_2$,
H-D-Cys-Phe-Phe-D-Trp-Lys-Thr-Phe-Cys-NH$_2$,
H-Cys-Phe-Trp-D-Trp-Lys-Ser-Phe-Cys-NH$_2$,
H-Cys-Phe-Phe-D-Trp-Lys-Ser-Phe-Cys-NH$_2$,
H-Cys-Phe-Phe-D-Trp-Lys-Thr-Phe-Cys-NH$_2$,
H-Cys-Phe-Tyr-D-Trp-Lys-Thr-Phe-Cys-NH$_2$,
H-Cys-Phe-His-D-Trp-Lys-Thr-Phe-Cys-NH$_2$,
H-Cys-Phe-Tyr(I)-D-Trp-Lys-Thr-Phe-Cys-NH$_2$,
H-D-Phe-Phe-Phe-D-Trp-Lys-Thr-Phe-Thr-NH$_2$; and mixtures thereof.

34. The method of claim 24, wherein the somatostatin type-5 receptor agonist comprises H-Cys-Phe-Phe-D-Trp-Lys-Thr-Phe-Cys-NH$_2$.

35. The method of claim 24, wherein the somatostatin type-5 receptor agonist comprises H-D-Phe-Phe-Phe-D-Trp-Lys-Thr-Phe-Thr-NH$_2$.

36. The method of claim 24, further comprising administering to the subject a therapeutic amount of an agent selected from the group consisting of bromocriptine, cabergoline, pergolide, lisoride and mixtures thereof.

37. A method of treating galactorrhea associated with levels of prolactin above a normal range, comprising conducting the method of claim 1.

38. A method of treating amenorrhea associated with high levels of prolactin above a normal range, comprising conducting the method of claim 1.

39. A method of treating infertility associated with high levels of prolactin above a normal range, comprising conducting the method of claim 1.

40. A method of treating impotence associated with high levels of prolactin above a normal range, comprising conducting the method of claim 1.

41. A method of treating hypergonadism a associated with high levels of prolactin above a normal range, comprising conducting the method of claim 1.

42. The method of claim 1, wherein the SSTR type-5 agent is administered as a composition further comprising a pharmaceutically acceptable carrier.

43. The method of claim 42, wherein the composition is in tablet, powder or liquid form.

44. The method of claim 42, wherein the composition further comprises an agent selected from the group consisting of biodegradable and sustained release polymers and further therapeutic agents selected from the group consisting of bromocriptine, cabergoline, pergolide, lisoride, and combinations thereof.

* * * * *

UNITED STATES PATENT AND TRADEMARK OFFICE
CERTIFICATE OF CORRECTION

PATENT NO. : 5,972,893
DATED : October 26, 1999
INVENTOR(S) : Shlomo Melmed, Ilan Shimon, Michael D. Culler It is certified that error appears in the above-identified patent and that said Letters Patent is hereby corrected as shown below:

ON THE TITLE PAGE:

[73] Assignees: Cedars-Sinai Medical Center, Los Angeles, Calif.
Biomeasure, Inc., Milford, Mass.

Signed and Sealed this

Thirty-first Day of October, 2000

Attest:

Q. TODD DICKINSON

Attesting Officer    Director of Patents and Trademarks